(12) United States Patent
    Zotz

(10) Patent No.: US 10,856,989 B2
(45) Date of Patent: Dec. 8, 2020

(54) DEVICE AND SYSTEM FOR AUGMENTING A HEART

(71) Applicant: Rainer Zotz, Metterich (DE)

(72) Inventor: Rainer Zotz, Metterich (DE)

( * ) Notice: Subject to any disclaimer, the term of this patent is extended or adjusted under 35 U.S.C. 154(b) by 0 days.

(21) Appl. No.: 15/527,594

(22) PCT Filed: Nov. 17, 2015

(86) PCT No.: PCT/EP2015/076894
§ 371 (c)(1),
(2) Date: May 17, 2017

(87) PCT Pub. No.: WO2016/079159
PCT Pub. Date: May 26, 2016

(65) Prior Publication Data
US 2017/0319343 A1    Nov. 9, 2017

(30) Foreign Application Priority Data
Nov. 17, 2014    (EP) .................................... 14193558

(51) Int. Cl.
*A61M 1/10*    (2006.01)
*A61F 2/24*    (2006.01)
*A61N 1/05*    (2006.01)
*A61M 1/12*    (2006.01)

(52) U.S. Cl.
CPC .......... *A61F 2/2481* (2013.01); *A61F 2/2478* (2013.01); *A61M 1/122* (2014.02); *A61N 1/0597* (2013.01); *A61M 1/106* (2013.01); *A61M 1/1068* (2013.01); *A61M 1/1086* (2013.01); *A61M 1/12* (2013.01)

(58) Field of Classification Search
CPC .............. A61F 2/24; A61M 1/10; A61M 1/12
See application file for complete search history.

(56) References Cited

U.S. PATENT DOCUMENTS

| | | | |
|---|---|---|---|
| 6,254,525 B1 | 7/2001 | Reinhardt et al. | |
| 6,808,483 B1 | 10/2004 | Ortiz et al. | |
| 2002/0058856 A1 | 5/2002 | Peng et al. | |
| 2003/0045771 A1 | 3/2003 | Cyril, Jr. et al. | |
| 2007/0106359 A1 | 5/2007 | Schaer et al. | |
| 2008/0064917 A1 | 3/2008 | Bar et al. | |
| 2008/0139873 A1 | 6/2008 | Peters et al. | |
| 2011/0092761 A1* | 4/2011 | Almog ................. | A61F 2/2481 600/16 |
| 2011/0196485 A1 | 8/2011 | Forsell | |

FOREIGN PATENT DOCUMENTS

| | | |
|---|---|---|
| AU | 2013231115 | 10/2013 |
| AU | 2013231115 | 10/2014 |
| WO | WO 2013/093074 | 6/2013 |

OTHER PUBLICATIONS

PCT Search Report and Written Opinion for application No. PCT/EP2015/076894 dated May 26, 2016.

* cited by examiner

*Primary Examiner* — Matthew W Schall
(74) *Attorney, Agent, or Firm* — Knobbe, Martens, Olson & Bear, LLP

(57) ABSTRACT

A radially compressible cardiac gripper for at least mechanical stimulation of a heart. The cardiac gripper has two gripper arms, wherein at least one of the gripper arms comprises a flexible section configured for movement of the arm having the flexible section.

19 Claims, 5 Drawing Sheets

DEVICE AND SYSTEM FOR AUGMENTING A HEART

This application is the U.S. National Phase under 35 U.S.C. § 371 of International Application No. PCT/EP2015/076894, filed Nov. 17, 2015, titled A DEVICE AND SYSTEM FOR AUGMENTING A HEART, which claims priority benefit to EP Patent Application No. 14193558.5, filed Nov. 17, 2014.

FIELD OF THE INVENTION

This disclosure pertains in general to the field of augmenting a heart. More particularly, the disclosure relates to a device and system for performing mechanical and/or electrical augmentation of a heart.

BACKGROUND OF THE INVENTION

Today different cardiac augmenting methods and devices are known, such as cardiopulmonary resuscitation (CPR) and a ventricular assist device (VAD).

When CPR is performed it can lead to complications that may need to be rectified. Common complications due to CPR are rib fractures, sternal fractures, bleeding in the anterior mediastinum, heart contusion, hemopericardium, upper airway complications, damage to the abdominal viscus, fat emboli, pulmonary complications—pneumothorax, hemothorax, lung contusions and so on. Additionally, in order to augment the heart with CPR over a longer time it preferably requires a number of people to conduct the CPR with a similar force due to each person becoming physically tired. Further, the CPR needs to be performed when a person is laying down on his/her back on a solid ground.

VADs are sometimes intended for short term use, typically for patients recovering from heart attacks or heart surgery, while others are intended for long-term use, typically for patients suffering from advanced congestive heart failure. VADs are designed to, mechanically by pumping, assist either the right (RVAD) or left (LVAD) ventricle, or both ventricles at once (BiVAD).

Known VADs are however constructed as complex devices which are quite intricate to implant into a patient. Thus, VADs are time consuming to implant and require surgeons and other highly trained clinical personal to implant them.

Further, since the VADs are connected directly to the blood stream for pumping the blood they also have common associated problems for devices with blood contact such as coagulation associated problems.

The VADs also have the problem of having moving parts, in particular supported by bearings, i.e parts which can fail and need to be replaced—which is complicated in an implanted device like a VAD.

Thus, a device, method and/or system which overcome the above drawbacks would be advantageous.

SUMMARY OF THE INVENTION

Accordingly, examples of the present disclosure preferably seek to mitigate, alleviate or eliminate one or more deficiencies, disadvantages or issues in the art, such as the above-identified, singly or in any combination by providing a device and a system for performing augmenting according to the appended patent claims.

According to a first aspect of the disclosure, a radially compressible cardiac gripper for at least mechanical stimulation of a heart, wherein the cardiac gripper comprises two gripper arms, and wherein at least one of the gripper arms comprises a flexible section configured for movement of the arm is disclosed.

According to a second aspect of the disclosure, a cardiac augmenting system comprising a radially compressible cardiac gripper for at least mechanical stimulation of a heart, wherein the cardiac gripper comprises two gripper arms, and wherein at least one of the gripper arms comprises a flexible section configured for movement of the arm and a means for pressurizing the cardiac gripper connected thereto.

Further examples of the disclosure are defined in the dependent claims, wherein features for the second and subsequent aspects of the disclosure are as for the first aspect mutatis mutandis.

Some examples of the disclosure provide for at least mechanical stimulation of the heart.

Some examples of the disclosure provide for an easy and reliable way to give mechanical stimulation for a long time.

Some examples of the disclosure are provided to (mechanically) assist the heart in its natural contractions and/or expansions.

Some examples of the disclosure are provided to improve and/or to restore a heart's movement (or a heart's blood pumping function) to a normal (related) degree of contraction and/or expansion.

Some examples of the disclosure provide for a radial compression which is low magnitude and/or force of pressure on the heart.

Some examples of the disclosure provide for a radial compression which is high in magnitude and/or force of pressure on the heart.

Some examples of the disclosure provide for a mechanism that allows for easy movement outwards and/or inwards for mechanically augmenting the heart.

Some examples of the disclosure provide for a space constrained movement mechanism.

Some examples of the disclosure provide for mechanical augmenting of the heart in a limited space, such as the inside of the thoracic cavity or pericardial cavity.

Some examples of the disclosure provide for not introducing any force to heart when the assist device is not functioning properly.

Some examples of the disclosure provide for a robust but still with a light weight construction.

Some examples of the disclosure provide for a device being flexible in a direction of corrugation and stiff in a direction perpendicular to the direction of corrugation.

Some examples of the disclosure provide for a better grip of the heart when augmenting the heart.

Some examples of the disclosure provide for a larger area of contact with the heart and thus the better grip.

Some examples of the disclosure provide for an attachment means to further improve the grip.

Some examples of the disclosure provide for attaching a device or part of a device to the heart without damaging the heart.

Some examples of the disclosure provide for a curvature giving a better grip when encompassing the heart and augmenting the heart.

Some examples of the disclosure provide for not damaging the heart mechanically.

Some examples of the disclosure provide for that a single diameter can be manufactured and/or selected in an emergency situation.

Some examples of the disclosure provide for a minimal damage when inserted around the heart for the mechanical stimulation.

Some examples of the disclosure provide for easy insertion around the heart.

Some examples of the disclosure provide for a pressure of a fluid will be quickly distributed.

Some examples of the disclosure provide for a best possible expansion and/or contraction.

Some examples of the disclosure provide for an ease of deployment.

Some examples of the disclosure provide for a pressure being more uniformly distributed.

Some examples of the disclosure provide for affecting an arm substantially simultaneously for pushing and/or pulling the arms away and/or together.

Some examples of the disclosure provide for acting as steering means.

Some examples of the disclosure provide for no leakage.

Some examples of the disclosure provide for booth handling and pressurisation.

Some examples of the disclosure provide for easy and more secure guidance into place around the heart.

Some examples of the disclosure provide for a stabile device.

Some examples of the disclosure provide for a self-balanced device.

Some examples of the disclosure provide for no need to produce a counter force, such as a torque or a twisting motion.

Some examples of the disclosure provide for a device arranged to account for an angled insertion.

Some examples of the disclosure provide for a device adapted to electrically stimulate and/or sense the electrical activity of the heart.

Some examples of the disclosure provide for a device configured to treat electrical conduction problems of the heart.

Some examples of the disclosure provide for measuring an intrinsic heart action.

Some examples of the disclosure provide for a device which supplants the rest of a mechanical or electrical, or in combination of, needed to obtain a normal cardiac output at rest or during exercise.

Some examples of the disclosure provide for a device configured for a cardioversion.

Some examples of the disclosure provide for a response to the pressure of the heart.

Some examples of the disclosure provide for sensing a counterforce.

Some examples of the disclosure provide for imaging.

Some examples of the disclosure provide for improved electrical contact.

Some examples of the disclosure provide for augmentation to be performed at any position around the heart.

Some examples of the disclosure provide for therapy can be performed at any position of the heart's surface.

Some examples of the disclosure provide for augmentation of the heart over a large area of the heart.

Some examples of the disclosure provide for individual augmentation.

Some examples of the disclosure provide for augmentation at different areas at, different times at different areas.

Some examples of the disclosure provide for augmentation at the same the time at different areas.

Some examples of the disclosure provide for mapping in 4D.

Some examples of the disclosure provide for finding inhomogenities which point to a source of fibrillation.

Some examples of the disclosure provide for ablation.

Some examples of the disclosure provide for detection of points to weak activation triggers in the heart.

Some examples of the disclosure provide for a device in emergency situations.

Some examples of the disclosure provide for a simple and quick insertion at the ribs.

Some examples of the disclosure provide for a deployment of a device or system by physicians and non-physicians within and outside the hospital.

Some examples of the disclosure provide for less invasive approaches.

Some examples of the disclosure provide for storing a part of a system above the stomach in the abdominal fat.

Some examples of the disclosure provide for an automated mechanical augmenting of the heart.

Some examples of the disclosure provide for a relaxed state such that a device or system does not introduce any force to the heart when the device or system is not in operation or not functioning.

Some examples of the disclosure provide for a cheap, compact and yet reliable heart function augmentation system.

Some examples of the disclosure provide for a reciprocating movement for heart support.

Some examples of the disclosure provide for an analysis in four dimensions, including time and a three-dimensional space.

Some examples of the disclosure provide for an alternating pressurization of a heart.

Some examples of the disclosure provide for a cardiac assist control based on pressure.

Some examples of the disclosure provide for a reciprocating squeezing movement on the heart for stimulating it.

Some examples of the disclosure provide for electrically stimulating the heart and/or means for detecting an electrical signal of the heart.

Some examples of the disclosure provide for treating electrical conduction problems of the heart.

Some examples of the disclosure provide for treating different kinds of electrical conduction problems automatically.

Some examples of the disclosure provide for controlling on a measured electrical activity of the heart and/or ECG.

Some examples of the disclosure provide for transmitting and/or receiving energy and/or data.

Some examples of the disclosure provide for a battery charging of the augmenting system.

Some examples of the disclosure provide for a telemetry component.

Some examples of the disclosure provide for automatic self-control and/or messaging and/or error messaging such as alert of replacement of a component, low heart pump function and other interesting common heart parameters or parameters of the device.

Some examples of the disclosure provide for an augmenting system completely implanted in a patient.

Some examples of the disclosure provide for a device produced with a 2D printer from biocompatible plastic.

Some examples of the disclosure provide for a device visible during X-ray, MRI and/or other imaging techniques.

Some examples of the disclosure provide for a method of temporarily treatment of the heart by at least augmentation.

Some examples of the disclosure provide for a method comprising augmenting the heart at systole and/or diastole.

Some examples of the disclosure provide for augmentation based on a control signal and the control signal is based on a sensor measurement.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of examples of the present disclosure, reference being made to the accompanying drawings, in which.

DETAILED DESCRIPTION OF THE INVENTION

Figure 1:
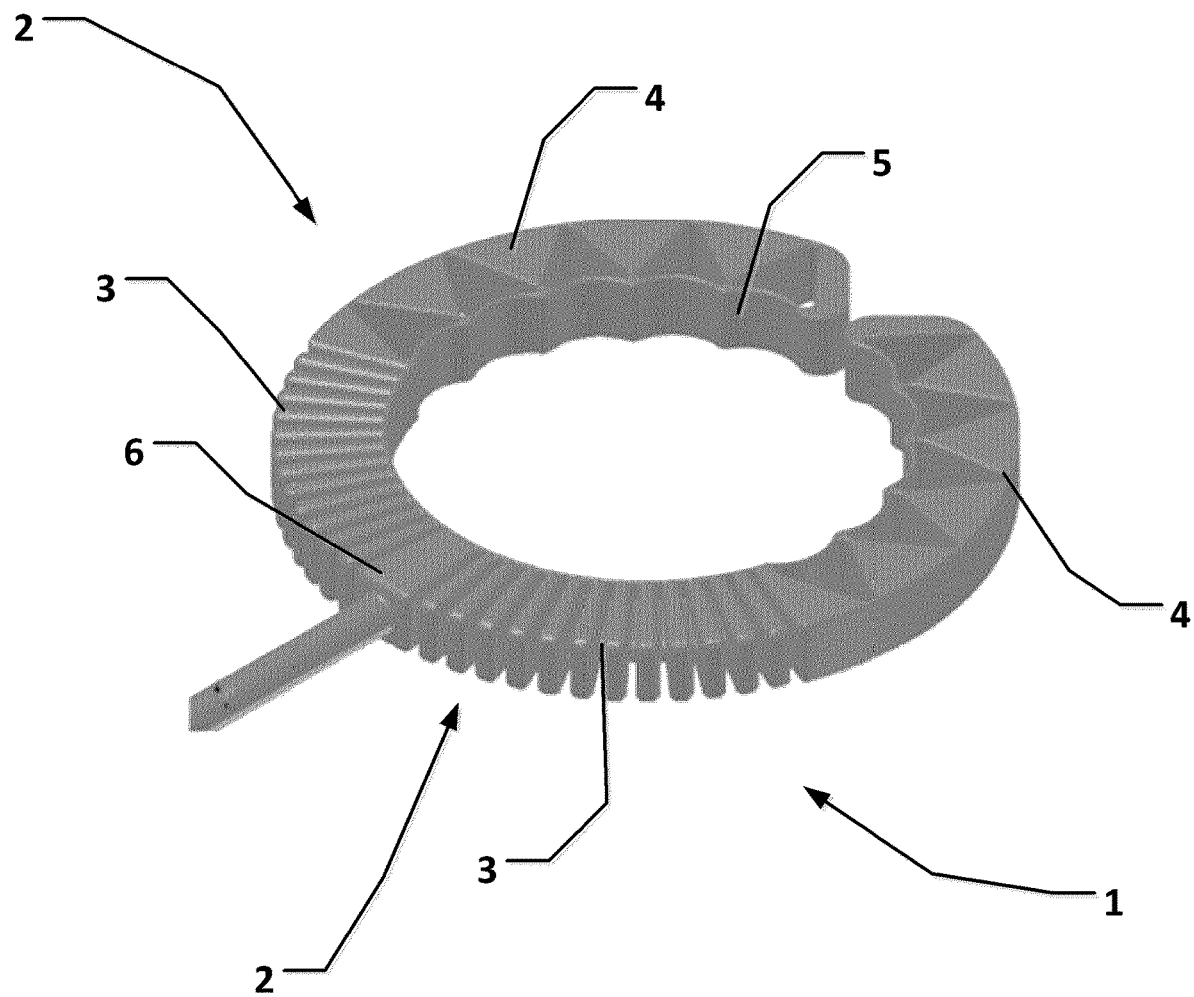
FIG. 1 is a schematic side view of an example of a cardiac augmenting device comprising at least one flexible gripper arm.

Specific examples of the disclosure now will be described with reference to the accompanying drawings. This disclosure may, however, be embodied in many different forms and should not be construed as limited to the examples set forth herein; rather, these examples are provided so that this disclosure will be thorough and complete, and will fully convey the scope of the disclosure to those skilled in the art. The terminology used in the detailed description of the examples illustrated in the accompanying drawings is not intended to be limiting of the disclosure. In the drawings, like numbers refer to like elements.

The following description focuses on an example of the present disclosure of a device for augmenting applicable to an organ and in particular to a heart. However, it will be appreciated that the disclosure is not limited to this application but may be applied to many other organs that pump or circulate fluids in a body including for example a lung. A "cardiac" gripper may thus be used for other organs as the heart, like a lung, for mechanical support thereof like the one described for the heart herein below.

Illustrated in FIG. 1, is an example of a radially compressible cardiac gripper 1 for at least mechanical stimulation of a heart. By having a radially compressible cardiac gripper 1 it is possible to give at least mechanical stimulation in an easy and reliable way for a long time.

Thereby, the cardiac gripper 1 is adapted to assisted the heart in its natural contractions and/or expansions and/or the heart can even be improved to restore it's movements to a normal degree of contraction and/or expansion if damaged. In an example, the cardiac gripper's 1 radial compression is low in magnitude and/or force since the pressure of the heart is low or high. In an example, the cardiac gripper's 1 radial compression is high in magnitude and/or force since the pressure of the heart is low or high.

In an example, the cardiac gripper 1 comprises two gripper arms 2 and wherein at least one of the gripper arms 2 comprises a flexible section 3 configured for movement of the arm 2. By having the gripper arms 2 comprising the flexible sections 3, the gripper arms 2 have a mechanism that allows the arms 2 to move easily outwards and/or inwards for mechanically augmenting the heart. In an example, the flexible section 3 is a concertinaed section. In an other example (not shown) only one of the gripper arms has such concertinaed section.

By having the concertinaed section 3 the gripper arms 2 have a space constrained movement mechanism built into the arms 2 which make them capable of moving outwards and/or inwards for mechanically augmenting the heart in a limited space, such as the inside of the thoracic cavity or pericardial cavity.

In an example, the cardiac gripper 1 is configured to have relaxed arms 2 such that they do not introduce any force to heart when not functioning, i.e. so that no harm is induced to the heart if the gripper 1 would fail.

In an example, at least one of the gripper arms 2 comprises a corrugated section 4. By having the corrugated section 4 the at least one arm 2 are made robust but still with a light weight construction.

In an example, the corrugated section 4 is flexible in a direction of corrugation and stiff in a direction perpendicular to the direction of corrugation.

In one example, the corrugations are described in terms of pitch (the distance between two crests) and depth (the height from the top of a crest to the bottom of a trough).

In an example, the pitch is between 1-15 and the depth is 1-50 mm and in an example the pitch is 5 and the depth is 2.5 mm.

Figure 2:
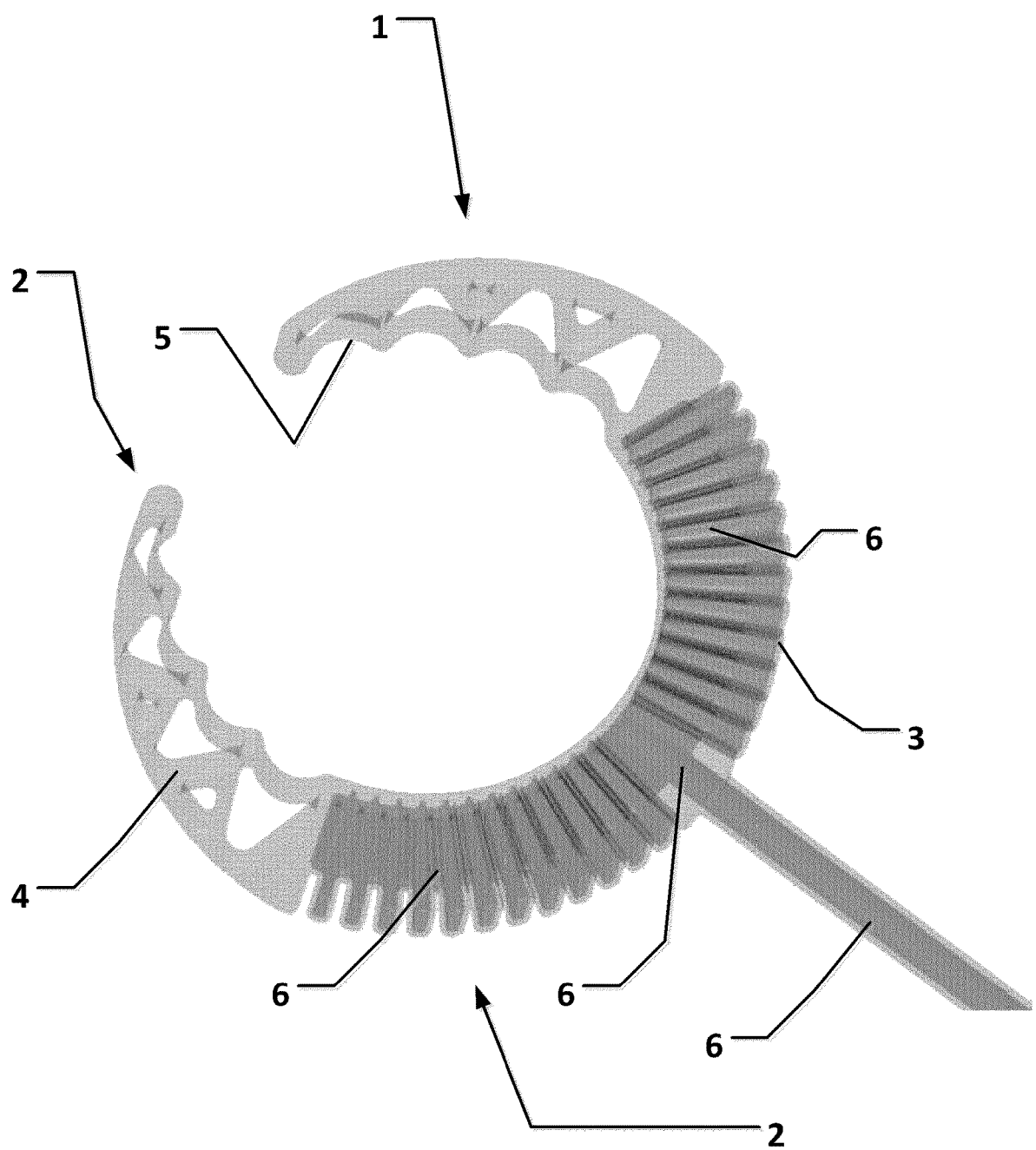
FIG. 2 is a schematic top view of an example of a cardiac augmenting device comprising at least one flexible gripper arm.

In another example, the corrugations are constructed of triangular solid and/or hollow triangular shapes, as e.g. illustrated in FIGS. 1-2. Other types of known shapes for constructing the corrugation are also possible such as, rectangular, sinusoidal and/or squared.

In an example, e.g. illustrated in FIGS. 1-2, at least one of the gripper arms 2 comprise a sinusoidal surface 5, and wherein the sinusoidal surface 5 is angled towards a centre point of the cardiac gripper 1. By having the sinusoidal surface 5 the at least one gripper arm 2 will have a better grip of the heart when augmenting the heart function. The sinusoidal surface 5 makes the gripper arms 2 have a larger area of contact with the heart and thus the better grip.

In an example, the epicardium or another location of the heart is attached to the cardiac gripper 1 by an attachment means to further improve the grip between the cardiac gripper 1 and the heart. Such attachment means is e.g. at least one suction cup, hook, glue or other known attachment means for attaching a device or part of a device to the heart without damaging the heart.

In an example, at least one of the gripper arms 2 are curved for a better grip when encompassing the heart and augmenting the heart. In an example, the curvature of the gripper arms 2 is chosen to be based on the interesting areas of compression, expansion and/or contraction of the heart. In an example, the curvature of the gripper arms 2 are chosen such that when the ends of the gripper arms 2 contact each other during the compression of the heart, the gripper arms 2 do not damage the heart mechanically, i.e. the inner diameter between the gripper arms 2 of the gripper 1 are larger than or substantially the same as a diameter of the heart, such as 60-80 mm.

Hence, a free space of the cardiac gripper 1 is equal to or larger than the diameter of the heart so that the augmentation device 1 cannot damage the heart by pushing the gripper arms 2 too tight around the heart when providing a maximum contraction.

Figure 3:
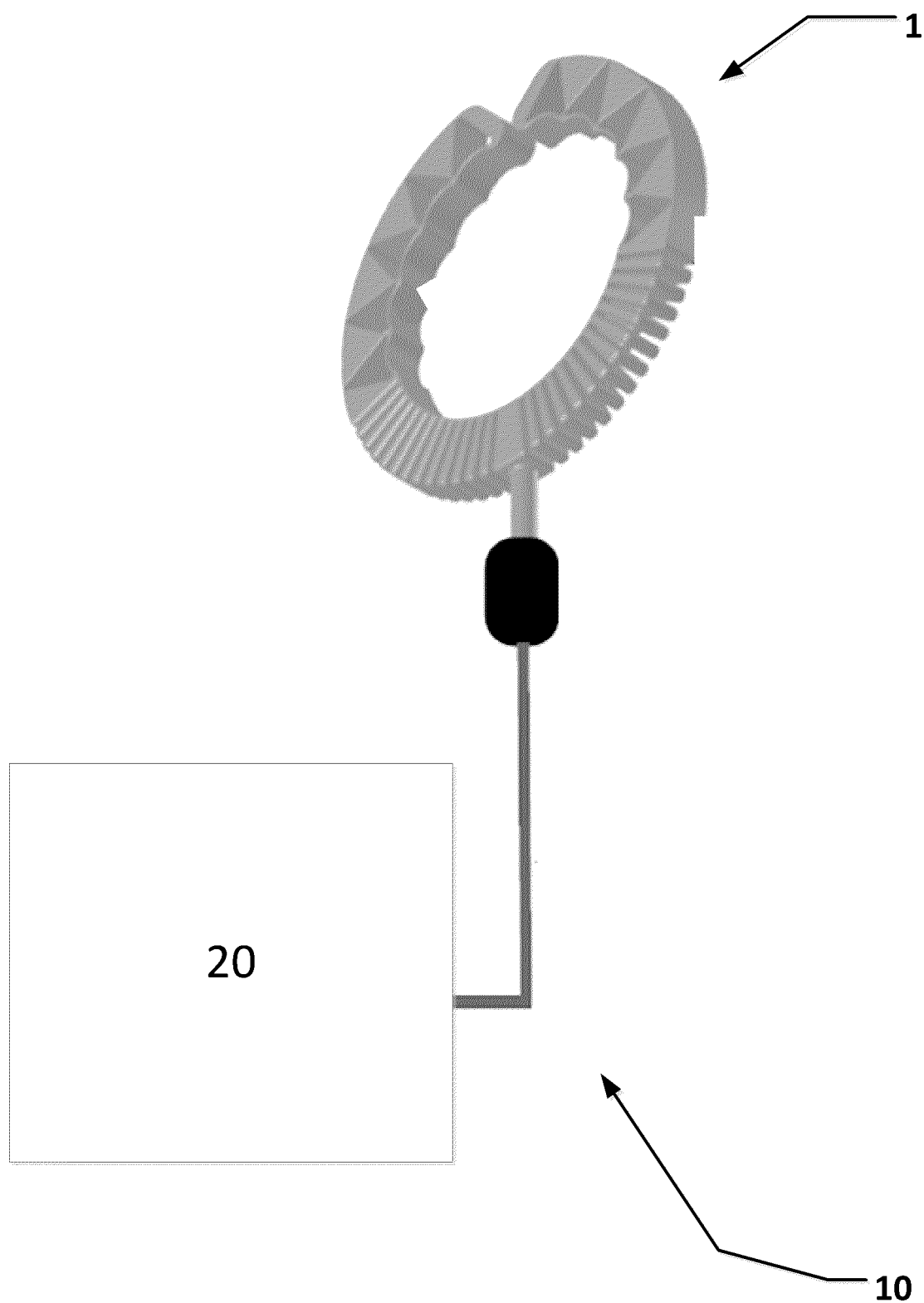
FIG. 3 is a schematic view of a cardiac augmenting system comprising a cardiac augmenting system and means for pressurising the cardiac augmenting system.

In addition or alternatively this means that the gripper arms 2 are configured to be have a stop of the motion when being in contact with their respective ends as e.g. illustrated in FIGS. 1 and 3.

In an example, the diameter of the gripper 1 is chosen to be equal to or larger than a diameter that is considered to be safe for most patients without damaging the heart of the same, such that a single diameter can be manufactured and/or selected in an emergency situation.

In an example, at least one gripper arm 2 is blunt at an end of the gripper arm 2. By having at least one gripper arm 2 blunt, or atraumatic at an end the gripper arm 2 will induce a minimal damage when inserted around the heart for the mechanical stimulation, as e.g. illustrated in FIG. 1.

In an example, at least one end of the gripper arm is angled at the end of the gripper arm. By having at least one end of the gripper arm angled the gripper arm 2 is easily inserted around the heart since the heart will be pushed into the centre of the gripper 1 and thus be aided by the angled end of the gripper arms 2, as e.g. illustrated in FIG. 1.

In an example, the cardiac gripper 1 comprises a fluid channel having an inlet 6 and wherein the inlet 6 is arranged at the gripper arms 2, e.g. illustrated in FIG. 2. By having the gripper 1 comprising the inlet 6 and the inlet 6 being arranged at the gripper arms 2, a pressure of a fluid in the fluid channel will be quickly distributed in the fluid channel in the arms 2 for pushing together or pulling away the gripper arms 2 from each other. In an example, the inlet 6 is adapted to be arranged anywhere on the cardiac gripper 1 for a best possible expansion and/or contraction of the gripper arms 2, ease of deployment of the gripper 1 and/or stability of the cardiac gripper 1.

In an example, the inlet 6 is arranged at a centre between the gripper arms 2. By having the inlet 6 at the centre between the gripper arms 2, a pressure from a fluid entering into the inlet 6 will be more uniformly distributed in the fluid channel in the arms 2 and thus affect the arms 2 substantially simultaneously for pushing and/or pulling the arms 2 away and/or together.

In an example, the fluid channel is integrated with and extending away from the cardiac gripper 1. In an example, the fluid channel is integrated with and extending away from the cardiac gripper 1 at the centre between the gripper arms 2. By having the fluid channel integrated with and extending away from the centre between the flexible sections 2, the fluid channel can also act as steering means for the cardiac gripper 1.

Further, there will be no leakage of the fluid at the gripper arms 2. In an example, the fluid channel is integrated with or coupled to a steering means such as a catheter, clamping device and other known steering devices such that booth handling, navigation and pressurising the cardiac gripper 1 is achieved.

In another example, the cardiac gripper 1 comprises an open end and wherein the open end is opposite of a centre between the gripper arms 2, i.e. the joining of the arms as illustrated in e.g. FIG. 1. By having the open end opposite the centre of the gripper arms 2, the gripper arms 2 can more easily and more securely be guided into place around the heart since the opening of the gripper 1 is arranged in a steering direction. Further, the cardiac gripper 1 is more stable when opening and closing since the cardiac gripper 1 is more or less self-balanced. Thus, an operator and/or other device steering and/or holding the cardiac gripper 1, does not need to produce a counter force, such as a torque or a twisting motion for holding the cardiac gripper 1 and the heart at its desired location.

In an example, the opening of the gripper 1 is adapted for a desired entrance point of the gripper 1 into a human or animal. Thus, the opening will be arranged such that the gripper 1 is inserted in e.g. an angle and the operator can just follow the angled direction and the gripper 1 will be arranged at its desired location around the heart 1 since the opening of the cardiac gripper 1 is arranged to account for the angled insertion.

In yet an example, the cardiac gripper 1 comprises means for detection of an electrical signal of the heart and/or means for stimulation of an electrical signal of the heart. By having the cardiac gripper 1 comprising means for detection of an electrical signal of the heart and/or means for stimulation of the electrical signal of the heart, the cardiac gripper 1 is adapted to electrically stimulate and/or sense the electrical activity of the heart.

In an example, the cardiac gripper 1 treats electrical conduction problems of the heart by e.g. defibrillation of the heart and/or ECG synchronized control of the heart.

In an example, the gripper 1 measures the intrinsic heart action mechanically and electrically and the gripper 1 supplants the rest of either modality, or in combination, of which is needed to obtain a normal cardiac output at rest or during exercise. If the heart is moving too slowly the gripper senses this and stimulates electrically and if there is no response augments mechanically. In an example, the gripper 1 performs a cardioversion.

In an example the cardiac gripper 1 comprises at least one pressure sensor that responds to the pressure of the heart. By having the pressure sensor the gripper 1 is adapted to sense a force from the heart motion and/or sense a counterforce when augmenting the heart mechanically such that e.g. the gripper 1 does not damage the heart by applying too high pressure to the heart.

In an example, the gripper comprises other types of sensors such as temperature sensors, accelerometers, ultrasound transmitters, ultrasound receivers, voltage sensors, potential sensors, current sensors, pH sensors, ECG sensors, ultrasound sensors or ablation sensors. One or more of these sensors may be integrated into the gripper, e.g. into a gripper arm, and arranged to directly or indirectly contact the exterior of the heart to be supported or mechanically massaged. Some of the sensors may be provided with a contact agent or displacement material, such as water or gel, since some transducers, such as ultrasound transducers, preferably should be located a small distance away from the heart wall for imaging and/or to give an improved electrical contact. In an example, the sensors are distributed at the gripper around the heart allowing for augmentation to be performed at any position around the heart covered by the gripper 1 and/or a net. In an example, electro-diagnosis and/or therapy can be performed at any position of the heart's surface. One or more of the sensors may also communicate, e.g. wirelessly, with a control unit of the gripper.

In an example, the gripper 1 comprises a mesh or net that is arranged around the heart and connected to the gripper 1. By having the net connected to the gripper 1, the gripper 1 and the net is adapted to augment the heart over a larger area of the heart. In an example the net is mechanically connected to the gripper 1, like a dip net, and follows the motion of the gripper 1.

In an example, the net and the gripper 1 are connected via a control unit, controlling them individually to augment the heart mechanically at different areas at, different times and/or at the same the time at different areas.

In example, the heart may have been lifted by a tool such as a spoon-shaped tool or catheter, and the gripper 1 and the net is then slid around the heart, so as to encompass at least a part of the heart. In an example, the sensors are comprised in the gripper arms 2 of the cardiac gripper 1. With the epicardial access and an additional the net or endocardial basket a simultaneous endocardial and epicardial mapping in 4D can be performed. The 4D mapping can thus find inhomogeneities which point to a source of fibrillation which in some cases can be ablated either endocardially or epicardially. In an example, endo-epi-gradients is detected and which points to weak activation triggers in the heart and the above may thus be treated with the gripper 1 and/or gripper 1 comprising the net.

In an example, the cardiac gripper 1 is configured to be deployed intercostally. By having the cardiac gripper 1 configured to be deployed intercostally it can be used in emergency situations by ambulance personnel which are then only required to make a simple and quick insertion at the ribs and the gripper 1 is following deployed through the ribs for augmenting the heart. Hence, the size of the cardiac gripper 1 is such that it will fit through the intercostal ribs space.

The implantation takes place through an opening in the skin and is normally less than 8 mm. However, other sizes of the opening are also possible, such as a typical incision ranging between 2-15 mm. It can be performed by physicians and non-physicians within and outside the hospital, analogous to the implantation of a chest tube.

In an example a method of delivering the cardiac gripper 1 and/or augmenting system 10 is disclosed. The method comprises an epicardial access approach or epicardial access surgery, subcostal access from the subxyphoid approach, and these are less invasive approaches than other approaches that can be used with e.g. VADs.

With the subcostal access, there is enough place above the stomach in the abdominal fat for storing associated devices to the gripper 1 such as means for pressurising the cardiac gripper 1, a motor, a battery, a control unit. The gripper 1 will then enter through and surround the heart from the apical southward origin.

In an example, the device 1 is also transluminally deliverable to the heart. A sheath or a catheter encompassing the gripper 1 is brought through the left arteria brachialis and advanced further to the target site. The target site may be a site, where the device 1 is in contact with, but exterior to the pericardial sack.

Figure 4:
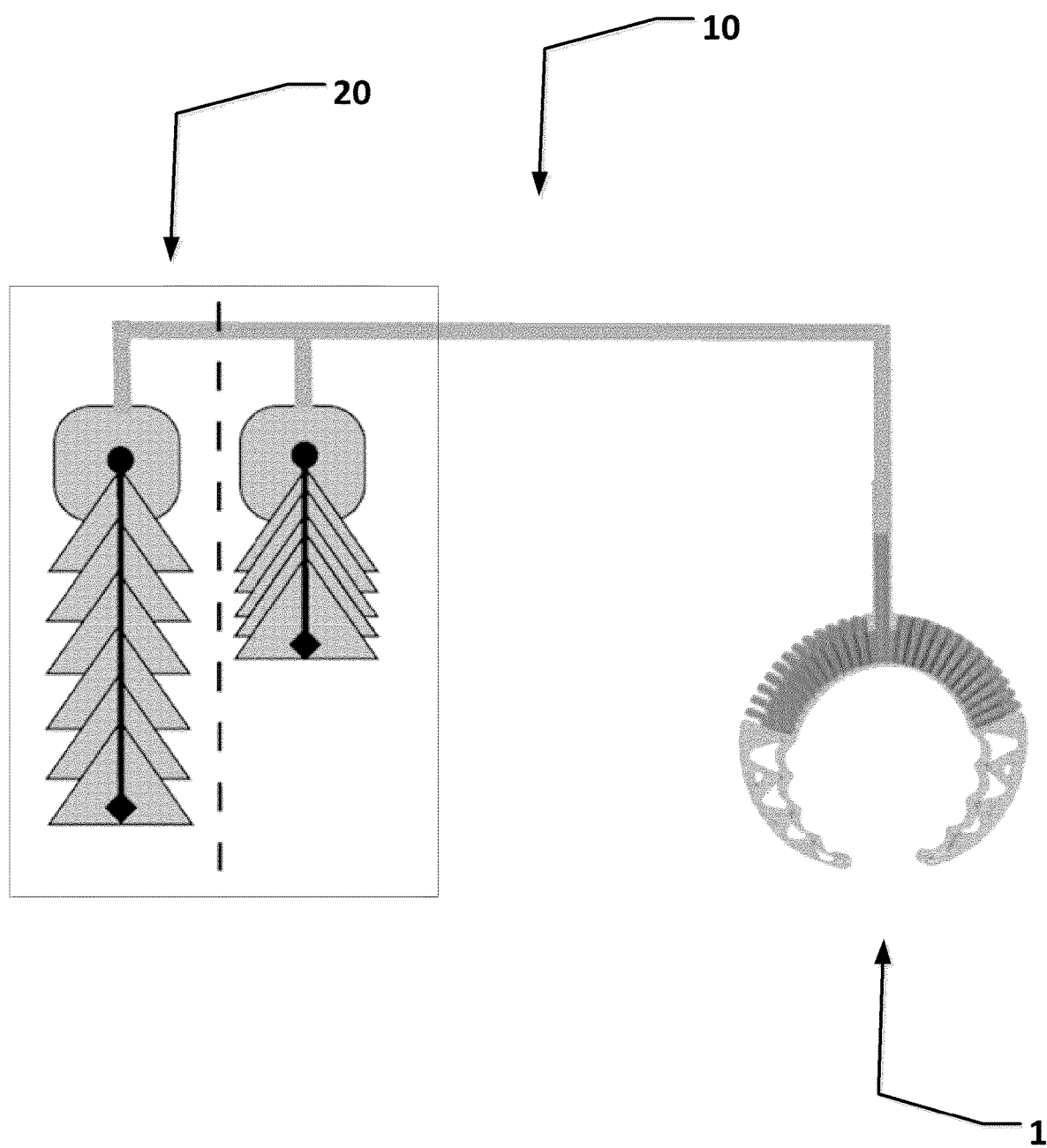
FIG. 4 is a schematic side view of a cardiac augmenting system comprising a cardiac gripper and means for pressurising the cardiac gripper. And, wherein the means for pressurising are illustrated in two of its pumping states, full and empty.

In an example, a cardiac augmenting system 10 is disclosed, e.g. illustrated in FIG. 3-4. The augmenting system 10 comprises a radially compressible cardiac gripper 1 for at least mechanical stimulation of a heart and a means for pressurizing 20 the cardiac gripper 1 connected thereto. By having the gripper 1 connected to the means for pressurizing 20 the gripper 1 it is possible to have an automated mechanical augmenting of the heart.

The means for pressurizing 20 is in an example one or several motors, one or several pneumatic actuators and/or one or several hydraulic actuators, such as a pump. If the means for pressurizing 20 is a pneumatic or hydraulic actuator, it is in an example located exterior to the body or in an example completely inside the body e.g. at the stomach as described above.

In an example, the augmenting system 10 is configured to be in a relaxed state such that the system does not introduce any force to heart when not functioning, i.e. so that no harm is induced to the heart if the gripper 1 or means for pressurizing would fail.

In an example, the means for pressurizing 20 is connected to an inlet 6 of the fluid channel arranged at a center between two gripper arms 2 of the cardiac gripper 1. By having the means for pressurizing 20 connected at the center between the gripper arms 2, an evenly distributed pressure will be achieved in the gripper 1 when it is pressurized so both arms 2 will be more or less affected at the same time.

As described above, in an example the gripper 1 comprises triangles, the analogue of a bellows which consist of an elastic section 3 and a corrugated section 4. As a result when inflated with compressed fluid such as air/gas and/or a fluid like sterile water, the gripper 1 will be moved in an expanding and/or contracting movement for massaging the heart for its blood pumping function.

In an example, the means for pressurizing the cardiac gripper 1 comprises a pressure tank formed of a flexible tube, and a step motor which is configured to compress and/or expand the flexible tube such that fluid flow towards and/or from the cardiac gripper 1. By having a flexible tube and a step motor a cheap, compact and yet reliable pressure solution, augmentation system 10, is achieved.

In an example, the augmenting system 10 comprises means for controlling the pressure of the means for pressurizing 20. By having means for controlling the means for pressurizing 20, the cardiac gripper 1 can be automated to move in a reciprocating movement, at diastole and/or systole. The gripper may be synchronized or controlled by a pulsating blood pressure to be obtained and/or measured. Measurement of the blood pressure may be done by known methods. A blood pressure signal may be provided to a control unit of the gripper as an input signal for a control feedback loop including actuation of the gripper for mechanical heart function augmentation.

Systole is the part of the cardiac cycle when the cardiac ventricles contract. The gripper thus may press on the heart muscle from its exterior and squeeze the heart ventricles towards the end diastolic point of the cardiac cycle. The gripper may also drag the ventricles inwardly depending on positioning to obtain or enhance the heart's contraction. Gripper pressure may be synchronized with heart function as described herein.

Diastole is the part of the cardiac cycle when the heart refills with blood following systole. The gripper may actively drag the ventricle outwardly when attached thereto. The gripper may also push the ventricles outwardly depending on positioning to obtain or enhance the heart's refilling expansion. Alternatively or in addition, the gripper passively relaxes to a end diastolic expanded position. Reciprocating motion then starts anew at the next systolic part of the subsequent cardiac cycle. Diastolic relaxation or expansion may be provided synchronized with heart function as described herein.

In an example, the means for controlling is an internal control unit such as an embedded device and/or in an example the means for controlling is an external control unit, such as a computer especially configured for a medical device. The means for controlling is in an example connected to another control unit by wires or wirelessly, and in an example can either or both of the means for controlling and other control unit also obtain measurements from sensors and/or control signals for controlling the gripper 1.

The controls signals sent may be measurement signals, such as measurement signals related to magnetic resonance imaging MRI or magnetic resonance tomography MRT. Another example of measurement signals is measurement signals related to an electrocardiogram. By sending measurement signals related to electrocardiograms continuously, an analysis in four dimensions, including time and a three-dimensional space, can be performed.

In an example, the means for controlling is configured to provide an alternating pressurization of the means for pressurizing 20. By alternating the pressurization the cardiac gripper 1 will open and close its arms 2, thus making a reciprocating squeezing movement on the heart for stimulating it.

In another example, the augmenting system 10 comprises means for electrically stimulating the heart and/or means for detecting an electrical signal of the heart. By having the cardiac augmenting system 10 comprising means for detecting and/or stimulating the electrical signal of the heart the system which thus also treats electrical conduction problems at the same time and/or by itself, as the gripper 1 gives mechanical stimulation.

In an example, the augmenting system 10 comprises means for controlling the means for stimulating the electrical stimulation the heart. By having means for controlling the electrical stimulation of the heart it is possible to treat different kinds of electrical conduction problems automatically. In an example, the means for controlling the electrical stimulation is, as with the means for controlling the pressure, connected by wires or wirelessly to another control unit.

In an example, the means for controlling the electrical stimulation is basing its control on a measured electrical activity of the heart and/or ECG. In an example, all the means described herein for controlling e.g. electrical stimulation or pressure (mechanical force of the gripper applied to the heart) is the same means for controlling.

In an example the augmenting system 10 comprises means for transmitting and/or receiving energy and/or data. By having the augmenting system 10 comprising means for transmitting and/or receiving energy, a battery charging of the augmenting system can be done wirelessly through the skin.

Further, by having means for transmitting and/or receiving data the system 10 is used in or as a telemetry component wirelessly. Thus, the augmenting system 10 may has automatic self-control and/or messaging and/or error messaging such as alert of replacement of a component, low heart pump function and other interesting common heart parameters or parameters of the device. In an example, the augmenting system 10 is completely implanted in a patient at the heart and at the stomach, as described above, or in an example at the heart and under the skin at the same place (shoulder pit) as like a pacemaker is implanted, and remotely wirelessly controlled to mechanically augment and/or electrically detect and/or stimulate the heart.

In an example, the heart gripper 1 is produced with a 3D printer from biocompatible plastic and which in an example comprises radiopaque iodine-containing substances or other substances for making the gripper 1 visible during X-ray, MRI and/or other imaging techniques.

Figure 5:
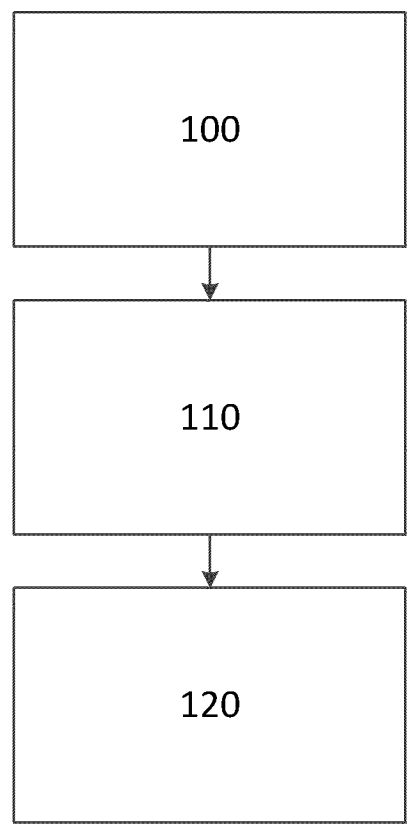
FIG. 5 is a flowchart of a method for augmenting using a cardiac augmenting system.

In an example, illustrated in FIG. 5, a method 100 of treatment by augmentation of the heart is provided. The method 100 comprises providing 110 a cardiac gripper 1 and moving 120 the cardiac gripper 1 for augmenting the heart. In an example, the method comprises augmenting the heart at systole and/or diastole.

In an example the providing 110 of the cardiac gripper 1 is easily performed by inserting the cardiac gripper 1 around the heart and this is due to the at least one gripper arm 2 comprising an angled end, as e.g. illustrated in FIG. 1. In another example, the cardiac gripper 1 is easily provided 110 at the heart by an open end of the cardiac gripper 1 and wherein the open end is opposite of a centre arranged between the gripper arms 2, i.e. the joining of the arms 2 as illustrated in e.g. FIG. 1. By having the open end opposite the centre of the gripper arms 2, the gripper arms 2 can more easily and more securely be guided into place around the heart since the opening of the gripper 1 is arranged in a steering direction of the cardiac gripper 1.

In an example the providing 110 comprises an operator to produce a counter force, such as a torque or a twisting motion for holding the cardiac gripper 1 at the heart, at its desired location.

In an example the providing 110 is by inserting the cardiac gripper 1 in e.g. an angle.

In an example, the providing 110 of the cardiac gripper 1 is performed by help of an integrated fluid channel or a fluid channel coupled to a steering mean such as a catheter, clamping device and other known steering devices such that booth handling, navigation and movement 120 of the cardiac gripper 1 is achieved.

In an example, the providing 110 of the cardiac gripper 1 is done by completely implanting the cardiac gripper 1 in a patient at the heart and at the stomach, as described above, or in an example at the heart and under the skin at the same place (shoulder pit) as like with a pacemaker.

In an example, the cardiac gripper 1 comprises a mesh or net that is also provided 110 around the heart. By having the net connected to the gripper 1, the gripper 1 and the net is adapted to augment the heart over a larger area of the heart. In an example the net is mechanically connected to the gripper 1, like a dip net, and follows the motion of the gripper 1. In an example, the net and the gripper 1 are connected via a control unit, controlling them individually to move 120 the heart mechanically at different areas at, different times and/or at the same the time at different areas.

In example, the heart may have been lifted by a tool such as a spoon-shaped tool or catheter, and the gripper 1 and the net is then provided 110 by sliding them around the heart, so as to encompass at least a part of the heart.

In an example the providing 110 is through an epicardial access. In an example the epicardial access allows for the cardiac gripper 1 comprising the net of performing a simultaneous endocardial and epicardial mapping in 4D. The 4D mapping can thus find inhomogeneities which point to a source of fibrillation which in some cases can be ablated either endocardially or epicardially. In an example, endo-epi-gradients is detected and which points to weak activation triggers in the heart and the above may thus be treated with the gripper 1 and/or gripper 1 comprising the net.

In an example, the cardiac gripper 1 is configured to and provided 110 to be deployed intercostal.

In an example the method of moving 120 the cardiac gripper 1 is performed when the natural contractions and/or expansions of the heart occur. In an example the method of moving 120 the cardiac gripper 1 is performed such that it substantially restores the heart's movements to a normal degree of contraction and/or expansion.

In an example, the moving 120 of the cardiac gripper 1 has a low magnitude and/or force. In an example, the cardiac moving 120 of the cardiac gripper 1 has a high magnitude and/or force.

In an example, the movement 120 is due to at least one of the gripper arms 2 comprising a flexible section 3 which allow the at least one arm 2 to move easily outwards and/or inwards for mechanically augmenting the heart.

In an example, the movement 120 of the cardiac gripper 1 is in a direction of a corrugation of the cardiac gripper 1. This is due to the cardiac gripper 1 comprising a corrugated section 4 which is flexible in a direction of the corrugation of the cardiac gripper 1. In an example the movement 120 is stiff in a direction perpendicular to the direction of corrugation.

In an example, the movement 120 of the cardiac gripper 1 is chosen to be based on an interesting area of compression, expansion and/or contraction of the heart.

In an example, the movement 120 of the cardiac gripper 1 of the at least one gripper arm 2 is chosen such that the movement if hindered from continuing by the ends of the gripper arms 2 contacting each other.

In an example, the movement 120 of the cardiac gripper 1 is due to the cardiac gripper 1 comprising a fluid channel for pressurising the cardiac gripper 1. In an example the movement 120 is achieved by having an inlet 6 and wherein the inlet 6 is arranged at the gripper arms 2, e.g. illustrated in FIG. 2. By having the gripper 1 comprising the inlet 6 and the inlet 6 being arranged at the gripper arms 2, a pressure of a fluid in the fluid channel will be quickly distributed in the fluid channel in the arms 2 for pushing together or pulling away the gripper arms 2 from each other.

In an example, the movement 120 of the cardiac gripper 1 is substantially simultaneously for pushing and/or pulling the arms 2 away and/or together.

In an example, the movement 120 if performed by the cardiac gripper 1 comprising the net.

In an example, the movement 120 of the cardiac gripper 1 is performed by a means for pressurizing 20 the cardiac gripper 1 connected thereto. By having the gripper 1 connected to the means for pressurizing 20 the gripper 1 it is possible to have an automated mechanical augmenting of the heart.

In an example one or several motors, one or several pneumatic actuators and/or one or several hydraulic actuators, such as a pump provides for the movement 120.

In an example the movement 120 of the cardiac gripper 1 is due to fluid filling and/or emptying the cardiac gripper 1 by help of the pressurising means 20.

In an example the movement 120 of the cardiac gripper 1 is due to the at least one motor pulling and/or pushing internally the cardiac gripper 1.

In an example, the movement 120 is in a reciprocating movement, at diastole and/or systole.

In an example, the method comprises regulating the augmentation based on a control signal. in an example the control signal is based on a sensor measurement, as also described above. In an example, the regulation is based on at least an electrical signal of the heart and/or means for stimulation of an electrical signal of the heart. In an example, the gripper 1 measures the intrinsic heart action mechanically and/or electrically and the gripper 1 supplants the rest of either modality, or in combination, of which is needed to obtain a normal cardiac output for an activity such as resting or during exercise.

In an example, the cardiac gripper 1 treats electrical conduction problems of the heart by e.g. defibrillation of the heart and/or ECG control of the heart. In an example, the heart is moving too slowly or to fast and the gripper senses this and stimulates electrically, but if there is no response the cardiac gripper 1 augments mechanically instead. In an example, the gripper 1 performs a cardioversion.

In an example the regulation of the cardiac gripper 1 is in response to the pressure of and/or from the heart.

In other examples, the cardiac gripper 1 is regulated by other types of sensors and/or signals therefrom such as temperature sensors, accelerometers, ultrasound transmitters, ultrasound receivers, magnetic resonance imaging (MRI), magnetic resonance tomography (MRT), voltage sensors, potential sensors, current sensors, pH sensors, ECG sensors, ultrasound sensors or ablation sensors. Some of the sensors may be provided with a contact agent or displacement material, such as water or gel, since some of the sensors, such as ultrasound, preferably should be located a small distance away from the heart wall for imaging and/or to give an improved electrical contact.

In an example, electro-diagnosis and/or therapy can be performed at any position of the heart's surface.

In an example the regulation is controlled by a specialised medical computer, a medical embedded computer or the like connected to the cardiac gripper 1 by wires or wirelessly.

In an example, the means for controlling is configured to provide an alternating pressurization of the means for pressurizing 20. By alternating the pressurization the cardiac gripper 1 will open and close its arms 2, thus making a reciprocating squeezing movement on the heart for stimulating its pumping action. In examples this is performed at predetermined times, for a duration of time or triggered by specific events detected in the sensor signals.

TABLE 1 comparison between different modalities

| Conventional CPR | Gripper Contraction |
|---|---|
| On solid ground only | Resuscitation without ground possible |
| Possible only in supine position | Possible in any posture, placement in supine and sitting position |
| Needs several persons over longer time | Needs only one person |
| Quality decreases with time | Quality remains stable |
| Complex procedure | Simple procedure |
| Remains in the hands of first rescuers | Can be transfered to a machine |
| Rib fracture is a must | No rib fracture |
| Pneumothorax possible | Pneumothorax possible |
| Difficult transport of patient | Simple transport of patient |
| Infection rare | Infection possible |
| Success rate < 20% | Success rate > 20% |
| Needs full concentration of rescuers | Automatic alarm with problems |
| In acute situation only | In acute and chronic situation |

| Conventional LVAD | Gripper contraction |
|---|---|
| Blood flow continuous | Blood flow pulsatile |
| Maximal flow 10 l | 20 l |
| Cannot defibrillate | Can defibrillate |
| Cannot cool | Is able to cool |
| Direct blood contact | No direct blood contact |
| Implantation time: 1-2 hours | Seconds |
| Innplanteur: surgeon and team | One primary care person |
| Possible complication: AI | Ø AI |
| Possible complication: Infection | Infection |
| Driveline: yes | Completely implantable with battery and TET |

TABLE 1-continued comparison between different modalities

| | |
|---|---|
| ECKG: no | Yes |
| Telemetry: yes | Yes |
| Completely implantable: no | Yes |
| Cost: >110.000 € | <500 € |
| Possible complication: stroke | Ø stroke |
| Induced coagulation abnormality: FVIII deficiency | No coagulation abnormality expected |
| Not applicable without specialized unit | Can be used everywhere (e.g. ambulance car) |
| Chronic application only | Chronic and acute application |
| Antikoagulation necessary | Anticoagulation not necessary |
| Durability several years | Durability unknown |
| Replacement very demanding | Replacement easy |
| Only LV support (+RV?) | LV + RV support |
| Right heart failure as possible complication | Right heart failure unlikely since both ventricles are supported |

The present disclosure has been described above with reference to specific examples. However, other examples than the above described are equally possible within the scope of the disclosure. The different features and steps of the disclosure may be combined in other combinations than those described. The scope of the disclosure is only limited by the appended patent claims. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

The invention claimed is:

1. A radially compressible cardiac gripper for at least mechanical stimulation of a heart adapted to be inserted around a heart muscle exterior, wherein the cardiac gripper comprises two opposed gripper arms in a single plane for mechanically massaging the heart in said plane, and wherein at least one of the gripper arms comprises a flexible section configured for movement of the arm in said plane, said movement being a movement on the heart for stimulating the heart at systole and/or diastole, wherein said gripper arms are adapted to provide said movement in said plane as a pressing movement during a systolic heart cycle phase on the heart muscle from its exterior and squeeze the heart ventricles, and/or wherein said gripper arms are adapted to provide said movement in said plane as a dragging or outwardly oriented pushing movement on the heart ventricles during a diastolic heart cycle phase and to obtain or enhance a refilling expansion of the heart.

2. The cardiac gripper according to claim 1, wherein at least one gripper arm is configured to be pressurized and moved by a fluid.

3. The cardiac gripper according to claim 2, wherein at least one of the gripper arms comprise a corrugated section.

4. The cardiac gripper according to claim 2, wherein at least one of the gripper arms comprise a sinusoidal surface, and wherein the sinusoidal surface is angled towards a center point of the cardiac gripper.

5. The cardiac gripper according to claim 2, wherein the cardiac gripper comprises a fluid channel having an inlet and wherein the inlet is arranged at the gripper arms.

6. The cardiac gripper according to claim 5, wherein the inlet is arranged at a center between the gripper arms.

7. The cardiac gripper according to claim 2, comprising an open end and wherein the open end is opposite of a center of the gripper arms.

8. The cardiac gripper of claim 1, wherein the cardiac gripper comprises means for detection of an electrical signal of the heart and/or means for stimulation of an electrical signal of the heart.

9. The cardiac gripper of claim 1, wherein the cardiac gripper is configured to be deployed intercostal.

10. A cardiac augmenting system comprising:
a radially compressible cardiac gripper for at least mechanical stimulation of a heart, said cardiac gripper adapted to be inserted around a heart muscle exterior of a heart; and
a means for pressurizing the cardiac gripper connected thereto for providing a movement on the heart, said movement being a movement on the heart for stimulating the heart at systole and/or diastole,
wherein:
said cardiac gripper is adapted to provide said movement as a pressing movement during a systolic heart cycle phase on the heart muscle from its exterior and squeeze the heart ventricles, and/or wherein said cardiac gripper is adapted to provide said movement as a dragging or outwardly oriented pushing movement on the heart ventricles during a diastolic heart cycle phase and to obtain or enhance a refilling expansion of the heart; and
said cardiac gripper is fail safe by being configured to have a relaxed state in which no force is introduced on the heart muscle when the cardiac gripper is not in operation.

11. The cardiac augmenting system according to claim 10, wherein the means for pressurizing is connected to an inlet of a fluid channel arranged at a center of a flexible section of the cardiac gripper.

12. The cardiac augmenting system according to claim 10, wherein the augmenting system comprises a means for controlling the pressure of the means for pressurizing.

13. The cardiac augmenting system according to claim 12, wherein the means for controlling the pressure is configured to provide an alternating pressurization of the means for pressurizing.

14. The cardiac augmenting system according to claim 10, wherein the augmenting system comprises a means for electrically stimulating the heart and/or means for detecting an electrical signal of the heart.

15. The cardiac augmenting system according to claim 10, wherein the augmenting system comprises a means for controlling the electrical stimulation the heart.

16. A cardiac augmenting system comprising:
a radially compressible cardiac gripper for at least mechanical stimulation of a heart, said cardiac gripper adapted to be inserted around a heart muscle exterior of a heart and including two opposed gripper arms in a single plane for said mechanical stimulation of said heart in said plane, wherein at least one of the gripper arms comprises a flexible section, and the gripper arms are configured to meet at ends thereof; and
wherein the augmenting system comprises a means for electrically stimulating the heart and/or means for detecting an electrical signal of the heart;
said system having a processing unit configured to stimulate the heart electrically if sensing that the heart is moving too slowly, and in absence of a response of the electrical stimulation mechanically stimulate said heart with said compressible cardiac gripper.

17. The system of claim 16, wherein said system includes at least one pressure sensor configured to respond to pressure of the heart and/or said gripper is configured to sense a force from motion of the heart and/or sense a counterforce when augmenting the heart mechanically.

18. The cardiac gripper according to claim 2, comprising a closed end where said two opposed gripper arms meet.

19. The cardiac gripper according to claim 1, comprising a holding element for an operator configured to hold the cardiac gripper and the heart at its desired location.

* * * * *